United States Patent
Benja-Athon

Patent Number: 5,961,453
Date of Patent: Oct. 5, 1999

[54] TANDEM IRREVERSIBLE COUPLING DEVICE IN ELECTROACUPUNCTURE

[76] Inventor: Anuthep Benja-Athon, 210 E. 36th St. Ground Floor, New York, N.Y. 10016

[21] Appl. No.: 09/185,108

[22] Filed: Nov. 3, 1998

[51] Int. Cl.$^6$ .................................................. A61B 17/34
[52] U.S. Cl. ............................................................ 600/372
[58] Field of Search .................................... 600/372, 373, 600/377, 382; 607/46, 48, 69, 70, 71, 74, 151; 606/189; 128/907

[56] References Cited

U.S. PATENT DOCUMENTS

| | | | |
|---|---|---|---|
| 4,055,190 | 10/1977 | Tany | 607/46 |
| 4,180,079 | 12/1979 | Wing | 607/69 |
| 5,387,231 | 2/1995 | Sporer | 607/48 |

Primary Examiner—George Manuel

[57] ABSTRACT

A first rigid plastic hood houses the end of the electrical lead comprises a hollow cavity wherein affixed an electricity-conducting cap holding the end of the electrical lead, a circular pawl at the fringe of the hood adaptable to end-to-end couple to the electricity-conducting head of the handle of a second independent electro-acupuncture needle wherein houses the end of the uninsulated, monopolar or bipolar shaft member which terminates in the electricity-conducting plate affixed to the top of the electricity-conducting head of the handle. The tandem irreversible coupling of the hood which is configured to fit the configuration of the head of the handle, to the head of the handle is achieved by a circular pawl at the fringe of the rigid plastic hood irreversibly latch onto the circular ratchet at the fringe of the electricity-conducting head of the second independent needle. Aforementioned coupling also resulted in the tight apposition of the electricity-conducting cap and the electricity-conducting plate for the optimal flow of electrical current from the electrical lead to the shaft of the needle to the tissues of a person or an animal in electroacupuncture. The irreversible coupling compels the disposal of the acupuncture needle and electrical lead after one single use.

11 Claims, 2 Drawing Sheets

TANDEM IRREVERSIBLE COUPLING DEVICE IN ELECTROACUPUNCTURE

FIELD OF INVENTION

Tandem irreversible coupling device to permanently unite electrical lead and electroacupuncture needle to prevent reuse of said lead and needle.

BACKGROUND OF THE INVENTION

This application provides a device for irreversible and tandem coupling of electrical lead and electro-acupuncture which is different from application Ser. No. 976,585 filed Nov. 24, 1997 titled Coupling Device In Electroacupuncture now U.S. Pat. No. 5,857,968 issued Jan. 12, 1999 to this applicant.

The first objective is to provide an means of irreversible and tandem coupling device in electroacupuncture to eliminate the transmission of infectious organisms such as bacteria, virus, fungus between patients and acupuncturists in electroacupuncture.

The second objective is to provide single-use, disposable, recyclable electrical lead and acupuncture needle and pin and to compel the disposable of all said instruments after their application on a patient in electro-acupuncture.

The third objective is to provide an easy-to-use, effective, reliable, fixed, i.e. immovable, coupling of the electrical lead and acupuncture needle and pin to ensure the ease and reliability of application and to achieve the above objectives.

The fourth objective is to provide effective, optimal, and reliable electrical connection and contact between the electrical lead and the acupuncture needle and, therefore, ensuring the correct and optimal delivery of electrical current from the electrical lead to the acupuncture needle and pin in electroacupuncture.

"Acupuncture has been used by millions of American patients and performed by thousands of physicians, dentists, acupuncturists, and other practitioners for relief of prevention of pain and for a variety of health conditions." (National Institutes of Health Consensus Development Statement. Acupuncture. Nov. 3–5, 1997). The United States Food and Drug Administration has classified acupuncture pin as a medical device. The approval and consensus have resulted in tremendous growth of the application of acupuncture therapeutics by American acupuncturists.

Lack of Sterile Equipment and Technique

Transmission of infections and diseases in electroacupuncture between patients and acupuncturists is well documented in the scientific literature (Ernst E. et al. Life-threatening adverse reactions after acupuncture? A systematic review. Pain 71: 123–126, 1997). Two of the reasons are that there is a lack of sterile equipment and technique and the disregards for using sterile equipment and technique. The design deficiency of the prior art of acupuncture pin and equipment significantly contributed to aforementioned problems.

Presently, electroacupuncture using the micron-thick shaft of a metallic needle and pin being grasped by a relatively larger alligator clip of one end of an electrical lead are the most commonly used tools used in America. Essentially, an acupuncture needle has a handle and a shaft with a bore and an acupuncture pin has a handle and a solid shaft. The electrical lead of prior art consisting of a plastic-insulated wire with one end connects to a grasping device such as an alligator clip and the opposite end connected to the electrical stimulator. To establish the flow of electrical current from the electrical lead to the shaft of the acupuncture needle, the alligator clip grasps onto the micron-thick shaft of the acupuncture needle for the purpose of transmitting electrical current from the stimulator via the wire, the grasping device, the acupuncture pin, into the patient.

First, the connection between alligator clip and the micron-thick shaft of the acupuncture needle and pin is loose and poor. The alligator clip is not designed for the purpose of grasping the micron-thin shaft of the acupuncture needle and pin whose diameter is too small to be effectively grasped by the alligator clip. As a result, unreliable delivery of correct ampere and voltage of the electrical current to the acupuncture needle and pin are common. Second, the contact parts of the alligator clip, after so many use, are often oxidized rendering the clip ineffective due to a barrier of a layer of nonconductive oxidized matters.

Breaching of the sterile technique is common. First, the alligator clip and the electrical lead, which are not sterile to start, will not fix to one position site of the shaft of the acupuncture needle and pin and will slide toward the acupuncture site of the skin during the application of the electrical lead leading to the contamination of the acupuncture skin site and, consequently, the transmission of infectious organisms via the acupuncture site of the skin. Second, the electrical lead and the alligator clip are reused from patient to patient. Eventhough the acupuncture needle and pin are sterile, the alligator clip and its electrical lead are not sterile.

In brief, the design deficiency of the acupuncture needle and pin and the electrical lead of prior art promotes the transmission infection and diseases between patients and acupuncturists. The present invention solves the aforementioned problems.

SUMMARY OF THE INVENTION

The design deficiencies of the prior art of acupuncture needle and pin and equipment significantly contributed to transmission of infections and diseases in electroacupuncture between patients and acupuncturists.

To overcome said deficiencies, the present invention is a first rigid plastic hood houses the end of the electrical lead comprises a hollow cavity wherein affixed an electricity-conducting cap holding said end of the electrical lead, a circular pawl at the fringe of the hood adaptable to end-to-end couple to the electricity-conducting head of the handle of a second independent electro-acupuncture needle wherein houses the end of the uninsulated, monopolar or bipolar shaft member which terminates in the electricity-conducting plate affixed to the top of the electricity-conducting head of the handle. The tandem irreversible coupling of said hood and said head is achieved by 1) the configuration of said hollow cavity perfectly fitting the configuration of said head of the handle and 2) by a circular pawl at the fringe of said hood adaptable to irreversibly latch onto the circular ratchet at the fringe of said head. Aforementioned coupling also resulted in the tight apposition of the electricity-conducting cap and the electricity-conducting plate for the optimal flow of electrical current from the electrical lead to the shaft of the needle to the tissues of a person or an animal in electroacupuncture. The irreversible coupling compels the disposal of the acupuncture needle and electrical lead after one single use. Thus, inadvertent puncture of the fingers and body parts of the acupuncturists is either reduced or eliminated.

PREFERRED EMBODIMENTS OF THE INVENTION

Figure 1:
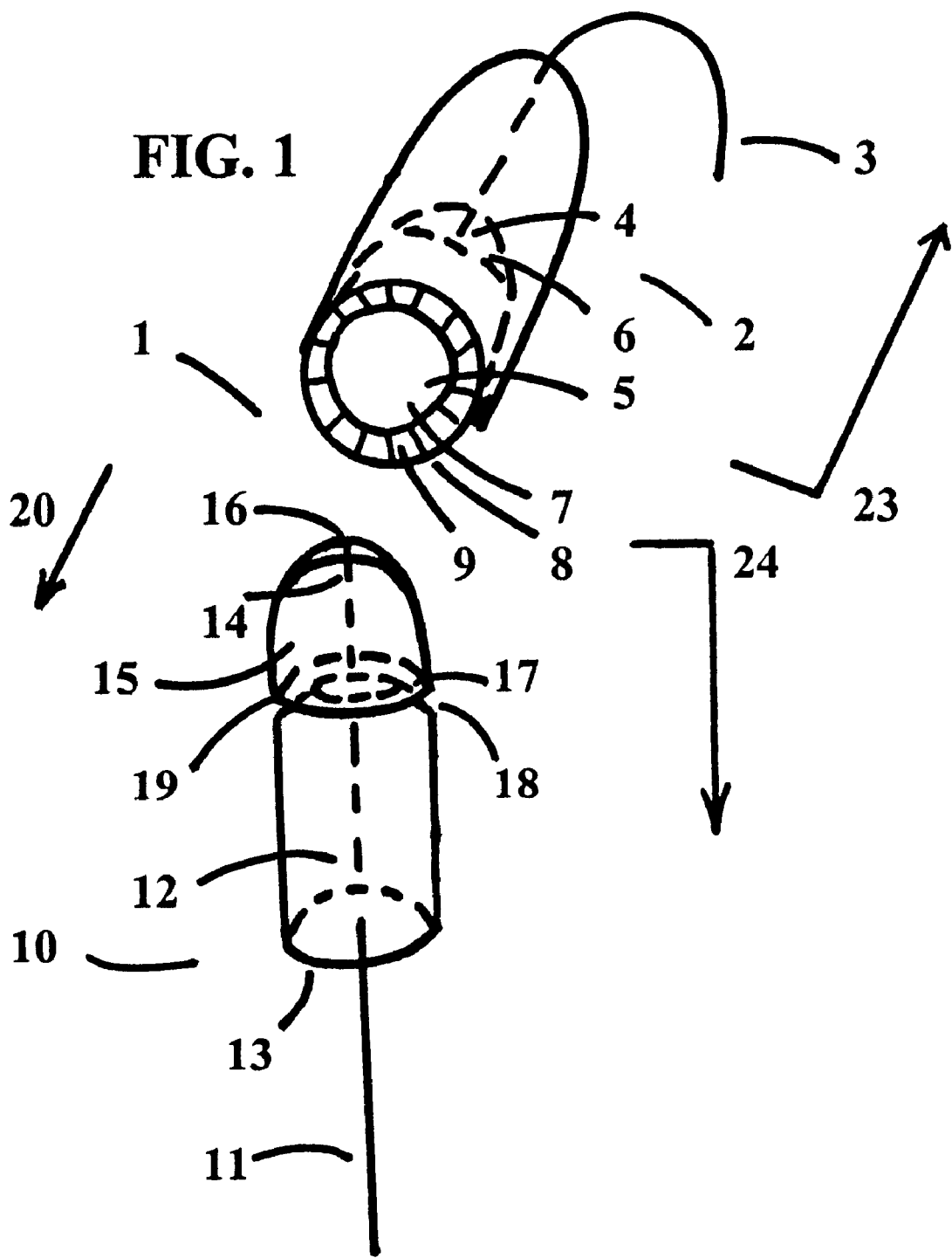
FIG. 1 is a perspective view of the present invention.

FIG. 1 shows the present invention 1 comprises a first independent hood 2 and a second independent electro-acupuncture needle or electro-acupuncture pin (henceforth referred to as needle) 10. Hood 2 is a retainer means of holding and housing one end 4 of the electrical lead 3 which ends in the hollow cavity 5 of hood 2 either as a free electricity-conducting electrical end (not shown) or within a first electricity-conducting surrogate means of conducting electricity which is an electricity-conducting metallic or alloy cap 6 housed in hollow cavity 5 and affixed to the ceiling of cavity 5. Cap 6 can also be affixed to other parts of the wall of cavity 5. Cap 5 is a thin piece of electricity-conducting metallic or alloy. Opening 7 into cavity 5 is formed by the circular fringe 8 of hood 2. Around fringe 8 is a circular pawl or a circular latch 9. Although in the drawings, hood 2 appears to be conical, however, other practical configurations of hood 2 include cylindrical. Other configurations of hood 2 and its component parts can be had as the preferred embodiments without departing from the spirit of the invention or the scope of the claims.

Needle 10 comprises an uninsulated, naked, electricity-conducting metallic or alloy monopolar or bipolar shaft member 11 and shaft member 12. The latter shaft 12 is within handle member 13 of needle 10 and continues into the head member 15 of needle 10 as a free end 14 (not shown) or an end within an electricity conducting metallic or alloy plate 16 which is affixed on the top of head member 15. The handle member 13 and head member 15 of needle 10 is configured like an erect straw-mushroom to have a circular rachet 17 at the fringe 19 of head member 15. As a result of said design and configuration of handle 13 and head member 15, circular notch 18 forms circular rachet 17. Electricity-conducting head member 15 is configured to end-to-end fit by invaginating said hollow 5 cavity and to end-to-end tightly appose the wall of said cavity 5. Other configurations and geometrical designs can be had of hood 2 including its components and needle 10 including its components without departing from the spirit of the invention or the scope of the claims.

During electroacupuncture, with strict sterile surgical technique, the electro-acupuncture needle 10 was percutaneously inserted through skin of a patient (not shown) and the tip of shaft 11 is positioned in the final desire position in the soft tissues of the patient. Hood 2 including cap 6 are designed and configured to precisely end-to-end fit needle 10 including head member 15 with plate 16 resulting in a tight tandem embrace of head 15 by cavity 5 and in optimal contact between cap 6 and plate 16. Alternatively, in settings wherein free end 4 of electrical lead 3 and free end 14 of shaft member 12 are configured and used with any or all said components, there is an optimal contact and a flow of electricity from electrical lead 3 which conduct electrical current from an electricity generating device to shaft members 12 and 11 into the tissues of a person or an animal.

Tandem irreversible coupling process can be initiated by end-to-end anastomosis of hood 2 to needle 10 by invaginating head member 15 bearing plate 16 into hollow cavity 5 whose ceiling is affixed with cap 6 as represents by single straight arrow 20. The ideal practical approach to said serial coupling, since handle 13 including head 15 is very small, is to move hood 2 to serially slid opening 7 of hollow cavity 5 over head member 15 until circular pawl 9 passing through circular trough 18 and irreversibly latch on to circular rachet 17. Said union indicates the irreversible engagement of circular pawl 9 and circular rachet 17 and that hood 2 has tightly embrace head member 15 resulting in the optimal contact between cap 6 and plate 16.

In order for the flow of electricity, cap 6 and plate 16 must be in contact. Alternatively, in aforementioned settings involving free ends, contact must be established between all said entities—cap 6, plate 16, ends 4 and 14 in any combination thereof. Said maximal contact is dictated by the design and configuration of hood 2 including its components and needle 10 including its components and that circular pawl 9 and circular rachet 17 must be irreversibly engaged.

Figure 2:
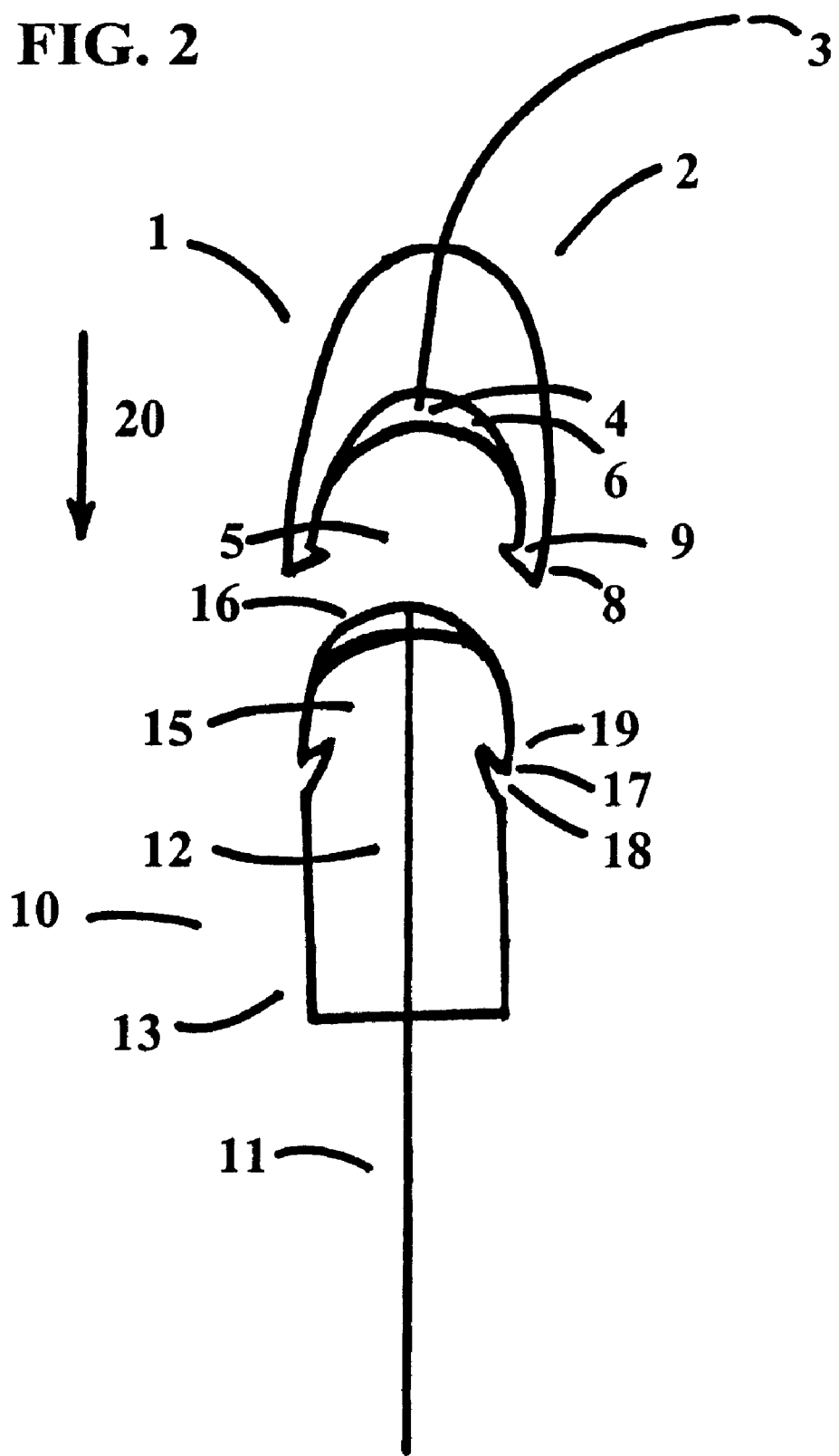
FIG. 2 is a schematic view of the present invention at section 23 and 24 in FIG. 1.

FIG. 2 shows the present invention 1, sectioned through the plane parallel to the paper of FIG. 1, comprises a first independent hood 2 and needle 10. Hood 2 is a retainer means of holding and housing one end 4 of the electrical lead 3 which ends in the hollow cavity 5 of hood 2 either as a free electricity-conducting electrical end (not shown) or within a first electricity-conducting surrogate means of conducting electricity which is an electricity-conducting metallic or alloy cap 6 housed in hollow cavity 5 and affixed to the ceiling of cavity 5. It is obvious from FIG. 2 that said tandem and irreversible coupling of hood 2 and needle 10 can be initiated by end-to-end anastomosis of hood 2 to needle 10 by invaginating head member 15 bearing plate 16 into hollow cavity 5 whose ceiling is affixed with cap 6 as represents by single straight arrow 20. Head member 15 comprises circular rachet 17 which engages circular pawl 9 which irreversibly latches on to circular rachet 17 through circular trough 18. Said union indicates the irreversible engagement of circular pawl 9 and circular rachet 17 and that hood 2 has tightly embrace head member 15 resulting in the optimal contact between cap 6 and plate 16.

After the electroacupuncture therapeutics, the irreversible couple hood 2—needle 10 is withdrawn as a single integrated unit from the skin and is discarded as one single unit. Therefore, no reuse of the electrical lead and the acupuncture needle is allowed.

Although various preferred embodiments of this invention have been described, it will be appreciated by those skilled in the art that adaptations and variations may be made without departing from the spirit of the invention or the scope of the claims.

I claim:

1. An irreversible end-to-end coupling device means for permanently uniting in tandem an independent electrical lead and an independent acupuncture needle to prevent the reuse of said lead and needle to reduce the risk of infection and the transmission of diseases in electro-acupuncture therapeutics comprising a first independent coupling means for irreversibly and tandemly coupling to a second coupling member means of said needle and an electricity-conducting surrogate means for holding an end of said lead and said second coupling member means for irreversibly and tandemly coupling to said first independent coupling means wherein said first independent coupling means is a retainer means of holding said end for said electrical lead within said electricity-conducting surrogate means comprising a head for conducting electricity within said first coupling means, wherein said second coupling member means is a serial and direct extension means of conducting electrical current of the handle of said needle, which comprises said handle, an uninsulated, monopolar or bipolar shaft having two ends wherein a first end of said shaft is the tip and the second end of said shaft is the opposite-to-said-tip end in an electricity-conducting means for conducting electrical current to said shaft wherewith, upon the application of electrical voltage to said lead and said first independent coupling means tandemly united to said second coupling member means, electrical current sequentially flows from said lead to said electricity-conducting surrogate means to said electricity-conducting means of conducting electrical current to said means of conducting electrical current of the handle to said shaft to the tissues of a person or an animal comprising:

contact means for conducting electrical current within said first independent coupling means.

2. The irreversible end-to-end coupling device means according to claim 1 wherein said first independent coupling member means is a rigid plastic hood comprising a hollow cavity and a fringe which defines the opening into said hollow cavity for retaining and housing said end of said electrical lead within said electricity-conducting surrogate means for holding an end of said lead, said hollow cavity is configured to accept and tandemly fit the configuration of said second coupling member means.

3. The electricity-conducting surrogate means for holding said end of said lead in claim 2 is an electricity-conducting metallic or alloy cap which is a thin piece of electricity-conducting metal or alloy affixed to and within said hollow cavity and configured to end-to-end fit the configuration of and tightly appose said an electricity-conducting means for conducting electrical current to said shaft.

4. The irreversible end-to-end coupling device means according to claim 2 wherein said second coupling member means is a serial and direct extension means for conducting electrical current of the handle of said needle to a head member of said handle comprising a circular rim housing said monopolar or bipolar shaft and configured to invaginate and tandemly fit said hollow cavity of said hood.

5. The irreversible end-to-end coupling device means according to claim 2 wherein said first independent coupling means is a circular pawl at a fringe of said hood configured to end-to-end fit the configuration of and to irreversibly latch onto said said second coupling means.

6. The irreversible end-to-end coupling device means according to claim 2 wherein said second coupling means is a circular ratchet at a rim of said head which is configured to end-to-end engage and fit said circular pawl at said fringe of said hood and to irreversibly latch onto said pawl.

7. The irreversible end-to-end coupling device means according to claim 3 wherein said contact means for conducting electrical current within said first independent coupling means is a electricity-conducting metallic or alloy cap which is a thin piece of electricity-conducting metal or alloy affixed to and within said hollow cavity.

8. The irreversible end-to-end coupling device means according to claim 4 wherein said electricity-conducting means for conducting electrical current to said shaft is configured to end-to-end fit and invaginate said hollow cavity of said hood and to tandemly and tightly appose said electricity-conducting cap within said hollow cavity of said hood.

9. The irreversible end-to-end coupling device means according to claim 3 wherein said electricity-conducting means for conducting electrical current to said shaft is a electricity-conducting plate affixed to said head wherein lies said opposite-to-said-tip end of said shaft and is configured to tightly and tandemly fit and appose said cap.

10. An irreversible end-to-end coupling device means for permanently uniting in tandem an independent electrical lead and an independent acupuncture needle to prevent the reuse of said lead and needle to reduce the risk of infection and the transmission of diseases in electro-acupuncture therapeutics comprising a first independent coupling means for irreversibly and tandemly coupling to a second coupling member means of said needle and said second coupling member means for irreversibly and tandemly coupling to said first independent coupling means wherein said first coupling member means has a retainer means of holding the end for said electrical lead, wherein said second coupling member means is a serial and direct extension means for conducting electrical current of a handle of said needle, wherein comprised in said handle, an uninsulated, monopolar or bipolar shaft having two ends wherein a first end of said shaft comprises a tip and a second end of said shaft comprises opposite-to-said-tip end with an electricity-conducting means for conducting electrical current to said shaft wherewith, upon the application of electrical voltage to said lead and said first independent coupling means tandemly united to said second coupling member means, electrical current sequentially flows from said lead to said electricity-conducting means for conducting electrical current and to said means of conducting electrical current.

11. The irreversible end-to-end coupling device means according to claim 10 wherein said retainer means for holding the end of said electrical lead comprises a rigid plastic hood with a hollow cavity and a fringe which defines an opening into said hollow cavity for retaining and housing said end of said electrical lead and said hollow cavity configured to accept and tandemly fit the configuration of said second coupling member means.

* * * * *